United States Patent [19]
Toutountzis et al.

[11] Patent Number: 5,927,024
[45] Date of Patent: Jul. 27, 1999

[54] TERMITE BARRIER

[75] Inventors: Vasilios Toutountzis, Sorrento; Laurence Graham Glossop, Duncraig, both of Australia

[73] Assignee: Termimesh Australia Pty. Ltd., Malaga, Australia

[21] Appl. No.: 08/925,972

[22] Filed: Sep. 9, 1997

[30] Foreign Application Priority Data

Sep. 9, 1996 [AU] Australia .................. PO2210

[51] Int. Cl.$^6$ ........................................ A01K 3/00
[52] U.S. Cl. ................................. 52/101; 52/292
[58] Field of Search ................. 52/101, 302.1, 52/302.3, 250, 292, 515, 728, 169.14, 517, 727

[56] References Cited

U.S. PATENT DOCUMENTS

| | | |
|---|---|---|
| 356,374 | 1/1887 | Parks . |
| 414,251 | 11/1889 | Phillips . |
| 539,485 | 5/1895 | Perret . |
| 985,681 | 2/1911 | Konopinski . |
| 1,201,756 | 10/1916 | Perry . |
| 2,017,106 | 10/1935 | Sandell ........................ 154/53 |
| 2,242,266 | 5/1941 | Scales ........................ 72/0.5 |
| 2,425,235 | 8/1947 | Ferrante ........................ 183/51 |
| 2,533,439 | 12/1950 | Elder ........................ 28/73 |
| 2,789,493 | 4/1957 | Riggle ........................ 52/302.1 X |
| 2,857,630 | 10/1958 | Bishop ........................ 20/4 |
| 2,899,771 | 8/1959 | Burris, Jr. ........................ 43/124 |
| 3,171,772 | 3/1965 | Lomar et al. . |
| 3,285,810 | 11/1966 | Hart ........................ 167/24 |
| 4,102,093 | 7/1978 | Harris ........................ 52/101 |
| 4,195,681 | 4/1980 | Douglas et al. ........................ 160/371 |
| 4,359,845 | 11/1982 | Harrison ........................ 52/302.3 X |
| 4,366,644 | 1/1983 | Lawrence ........................ 43/132 R |
| 4,547,626 | 10/1985 | Pedersen et al. ........................ 174/107 |
| 4,635,393 | 1/1987 | Pfeffer, Sr. et al. ........................ 43/112 |
| 4,636,543 | 1/1987 | Helton ........................ 524/109 |
| 4,667,436 | 5/1987 | Benson ........................ 43/132.1 |
| 4,678,699 | 7/1987 | Kritchevsky et al. ........................ 428/175 |
| 4,823,520 | 4/1989 | Ebeling et al. ........................ 52/101 |
| 5,094,045 | 3/1992 | Tamashiro ........................ 52/101 |
| 5,417,017 | 5/1995 | Toutountzis ........................ 52/101 |

FOREIGN PATENT DOCUMENTS

| | | |
|---|---|---|
| 4707/91 | 5/1963 | Australia . |
| 64977/69 | 6/1971 | Australia . |
| A-85176/82 | 6/1981 | Australia . |
| A-11412/1983 | 2/1983 | Australia . |
| A-21924/83 | 2/1983 | Australia . |
| A-16980/83 | 7/1983 | Australia . |
| S-125408 | 12/1995 | Australia . |
| 24980/95 | 1/1996 | Australia . |
| 27242/95 | 1/1996 | Australia . |
| S-126397 | 4/1996 | Australia . |
| 41004/97 | 1/1997 | Australia . |
| 58337/96 | 1/1997 | Australia . |
| A-58337/96 | 1/1997 | Australia . |
| 23741/96 | 12/1997 | Australia . |
| 28583/97 | 1/1998 | Australia . |
| 596093 | 2/1925 | France ........................ 52/101 |
| 2 453 952 | 2/1979 | France . |
| 19554 | 9/1994 | WIPO ........................ 52/101 |

OTHER PUBLICATIONS

Preventing Damage to Building by Subterranean Termites and Their Control, Farmers Bulletin, #1911, U.S. Department of Agriculture, Nov. 1942.
Product Sample, EHWA Wire Cloth Co., Ltd.
Stainless Steel Wire Cloth, EHWA Wire Cloth Co., Ltd.
Les Termites Et La Protection Des Constructions, Cahiers Du Centre Scientifique Et Technique Du Batiment 1950.

Primary Examiner—Creighton Smith
Attorney, Agent, or Firm—Kinney & Lange, P.A

[57] ABSTRACT

A termite barrier (30) particularly suitable for protecting buildings which have a concrete slab (15) with an object such as a conduit (11) extending through an opening (13) in the slab. The termite barrier (30) comprises a body (31) having a sleeve (33) defining an aperture (35) extending therethrough to sealingly receive the conduit (11). The body (31) has an outer peripheral portion defining a flange portion (37) adapted to be integrally secured to the concrete slab (15). The flange portion (37) is provided with means (43) for gripping engagement with the concrete structure.

19 Claims, 9 Drawing Sheets

TERMITE BARRIER

BACKGROUND OF THE INVENTION

The present invention relates to the control of termites in relation to buildings and other structures and in particular provision of a termite barrier between a structure (such as a concrete slab) and an object (such as a conduit) extending therethrough.

U.S. Pat. No. 5,417,017, the contents of which are incorporated herein by way of reference, discloses techniques for protecting a building or like structure against the entry of termites using termite barrier material. The disclosure includes an arrangement for preventing the passage of termites through a gap which might exist between an opening in a concrete slab and a conduit accommodated within the opening to extend through the concrete slab. The arrangement comprises a sleeve of barrier material which is, in use, located about the periphery of the conduit and clamped in pressure engagement therewith about the complete perimeter of the conduit, and an integral flange formed of said barrier material projecting from said sleeve, the integral flange in use being sealably embedded in the slab.

Embedding at least part of the flange in the concrete is a particularly convenient way of attaching the barrier material to the concrete slab.

SUMMARY OF THE INVENTION

It has now been found that the integral connection between the termite barrier and the concrete can be achieved by providing the flange with means which facilitates gripping engagement with the concrete.

Accordingly, the present invention provides a termite barrier comprising a body having an inner peripheral portion defining an aperture extending therethrough to sealingly receive an objet therein and an outer peripheral portion adapted to be integrally secured to a concrete structure, the outer peripheral portion being provided with means for gripping engagement with the concrete structure.

The body may sealingly receive the object in the aperture in any suitable fashion. In one arrangement, the aperture may be dimensioned to provide a sufficiently close fit between the body and the conduit to prevent the passage of termites through the aperture. In another arrangement, the body may be in sealing engagement with the object. In the latter arrangement, the sealing engagement may be in any suitable form such as frictional engagement or pressure engagement achieved by a clamping action applied to the body.

The outer peripheral portion may be embedded entirely in the concrete or a section thereof only may be embedded in the concrete.

The means for gripping engagement may comprise a surface of the outer peripheral portion configured for gripping engagement with the concrete structure in which it is in use embedded to provide sealing therebetween against the entry of termites. The configuration of the surface may provide keying between the flange portion and concrete.

The gripping engagement between the outer peripheral portion and the concrete maintains the integrity of sealing between the outer peripheral portion and the concrete in circumstances where the concrete is subject to normal shrinkage.

The outer peripheral portion may comprise a flange portion.

The inner peripheral portion of the body may comprise a sleeve which surrounds and defines the aperture. The sleeve and flange portion may be formed integrally with each other.

The flange portion may be provided with a formation which facilitates gripping engagement between the flange portion and the concrete structure. The formation may be of any suitable form, including perforations, dimples or some other type of recess or recesses provided in the flange or one or more protrusions on the flange such as annular ribbing on the flange.

In this arrangement, the flange portion may have a pair of opposed surfaces of generally planar form, the formation being on at least one of the opposed surfaces.

The termite barrier may be of any suitable material such as metal or plastics material. If the material is of a type not resistant to termite attack, that portion of the termite barrier which bridges the gap between the conduit and the surrounding concrete is preferably configured so as not to present a surface on which a termite can maintain a continuous physical grip. In this way, termites cannot remain in contact with said portion of the termite barrier for sufficient time to be destructive to the barrier to an extent which renders it ineffective.

The invention further provides in combination with a building structure incorporating a ground level or near ground level concrete structure having an opening therein through which an object (such as a conduit) extends, a termite barrier comprising a body having an inner peripheral portion defining an aperture extending therethrough to receive the object in sealing engagement therewith and an outer peripheral portion adapted to be integrally secured to a concrete structure, the outer peripheral portion being provided with means for gripping engagement with the concrete structure.

The invention also provides a method of establishing a termite barrier between a concrete structure having an opening therein and an object extending through the opening, the termite barrier comprising a body having an inner peripheral portion defining an aperture extending therethrough to receive the object and an outer peripheral portion provided with means for gripping engagement with the concrete structure, the method including the steps of embedding at least part of the flange portion in the concrete structure during pouring of the concrete thereof, and positioning the object in the aperture in sealing engagement therewith.

BRIEF DESCRIPTION OF THE DRAWINGS

The invention will be better understood by reference to the following description of several specific embodiments thereof as shown in the accompanying drawings in which.

DETAILED DESCRIPTION OF THE PREFERRED EMBODIMENTS

Figure 1:
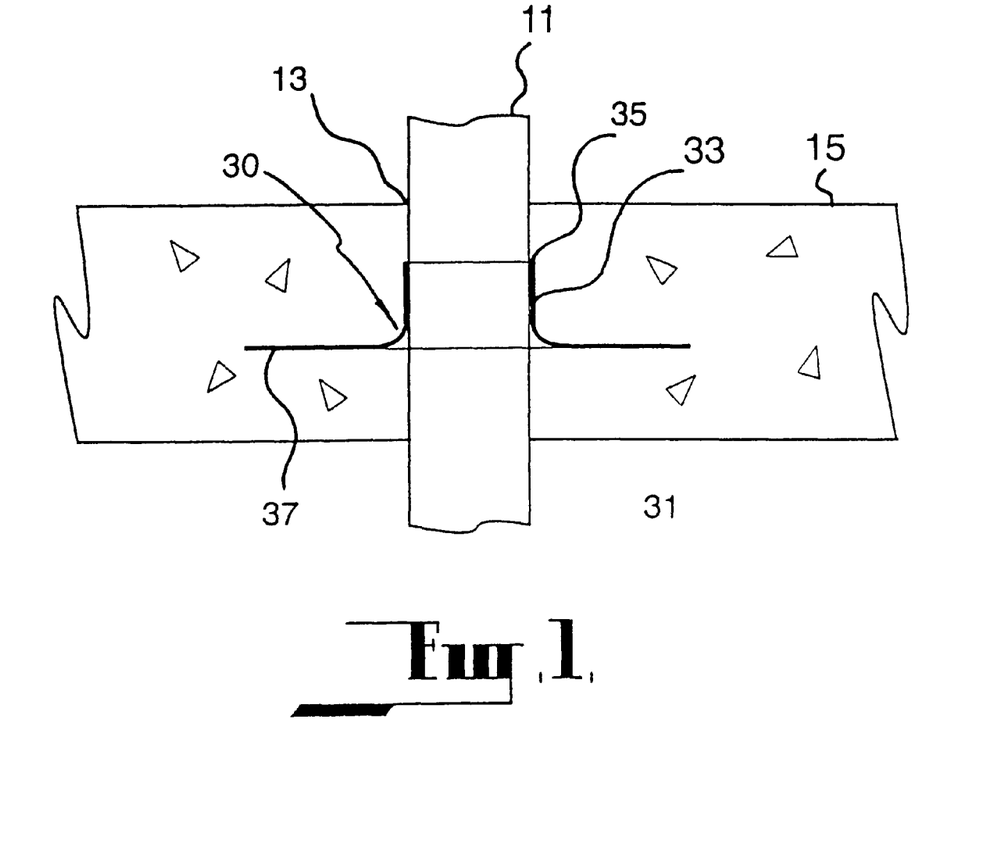
FIG. 1 is a schematic view of a termite barrier according to a first embodiment installed about a conduit extending through a concrete slab.

Referring to FIG. 1, there is shown a conduit 11, such as a water or waste pipe, positioned within an opening 13 within a concrete slab 15 so as to extend through the slab. The opening 13 in the slab 15 is a potential avenue for the passage of termites into a building structure standing on the slab. A termite barrier 30 according to the first embodiment is provided to block the passage of termites between the conduit 11 and the slab 15.

The termite barrier 30 according to the first embodiment comprises a body 31 of substantially rigid material such as metal or a hard plastics material.

Figure 2:
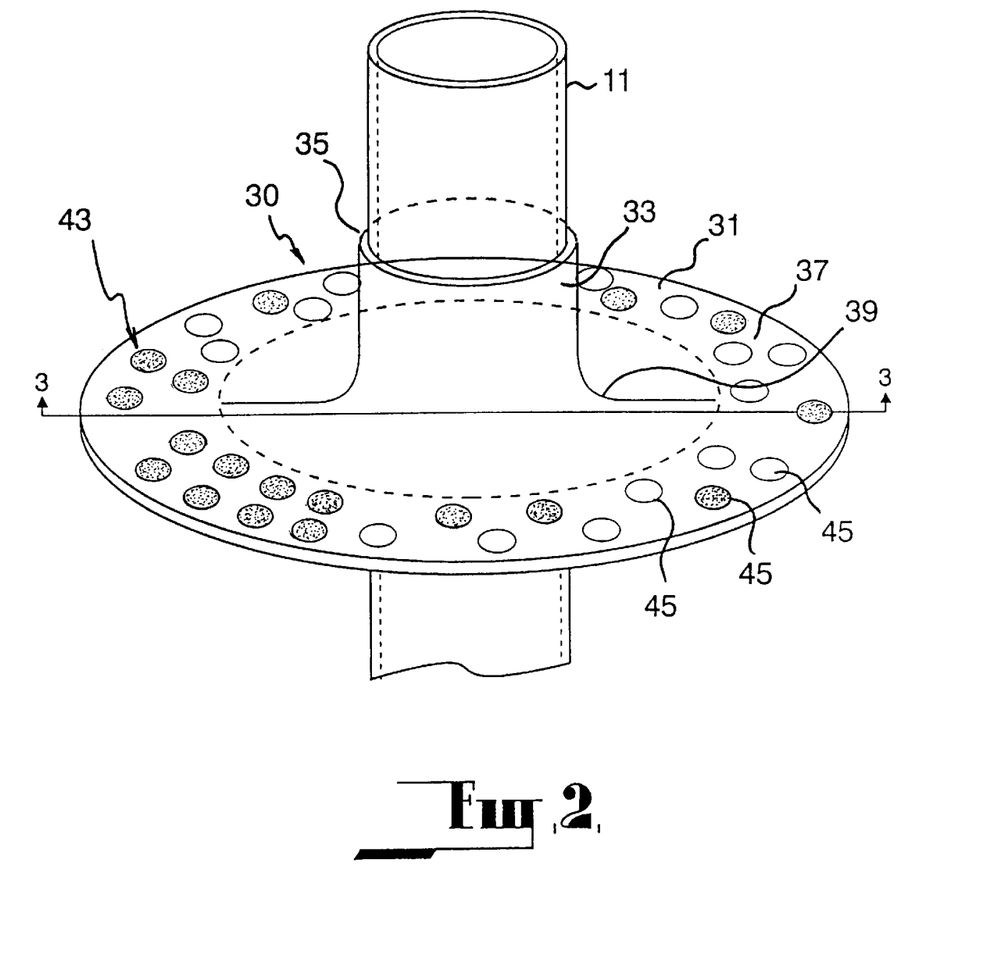
FIG. 2 is a schematic perspective view of a termite barrier according to the first embodiment fitted onto a conduit.
Figure 3:
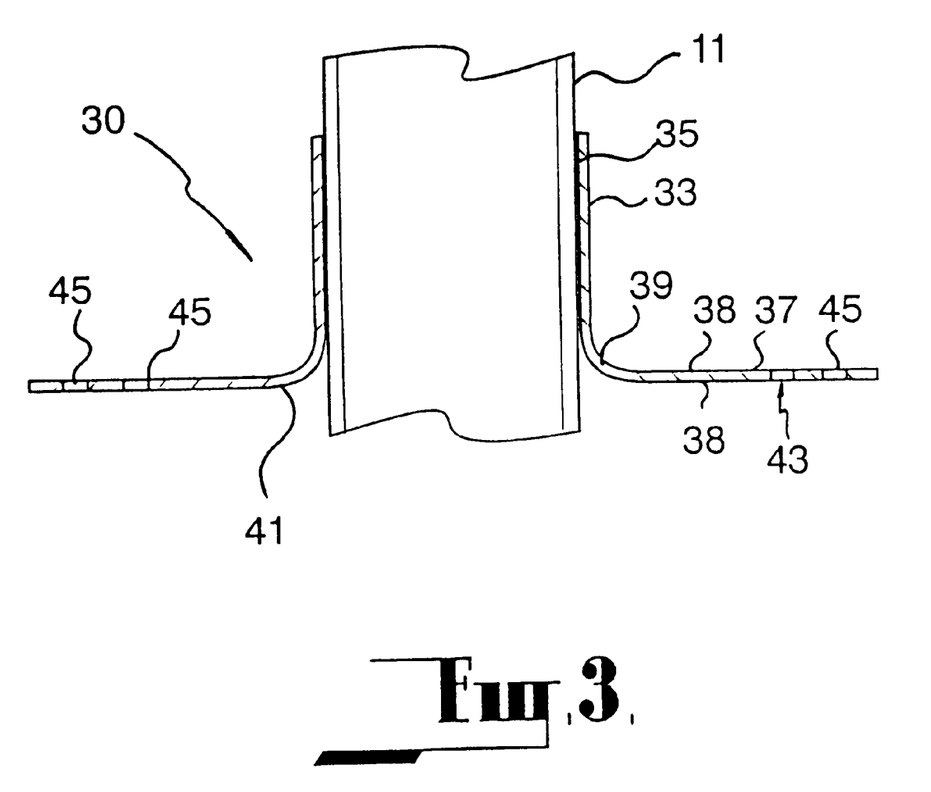
FIG. 3 is a section along line 3–3 of FIG. 2.

The body 31 incorporates a central sleeve 33 defining a central aperture 35 for receiving the conduit 11. An integral flange portion 37 surrounds the sleeve 33 and projects outwardly therefrom. The flange portion 37 has a pair of opposed planar faces 38.

The transition region 39 between the sleeve 33 and the flange portion 37 is arcuate so as to present a convex surface 41 on the lower side.

In circumstances where the material from which the body 31 is formed is not resistant to termites, the radius of curvature of the convex surface 41 is sufficiently large so that it cannot be gripped by a termite. This ensures that the portion of the barrier bridging the gap between the conduit 11 and the opening in the slab through which the conduit extends cannot be degraded by attack from termites.

That part of the flange portion 37 which is to be embedded in the concrete of the slab incorporates a formation 43 for gripping engagement with the concrete. The formation 43 comprises a plurality of holes 45 in the flange portion into which the concrete can flow prior to setting thereof. Once the concrete has set, keying between the concrete and the flange portion 37 provided by the presence of concrete in the holes 45 ensures gripping engagement therebetween and thus an effective termite seal.

Figure 4:
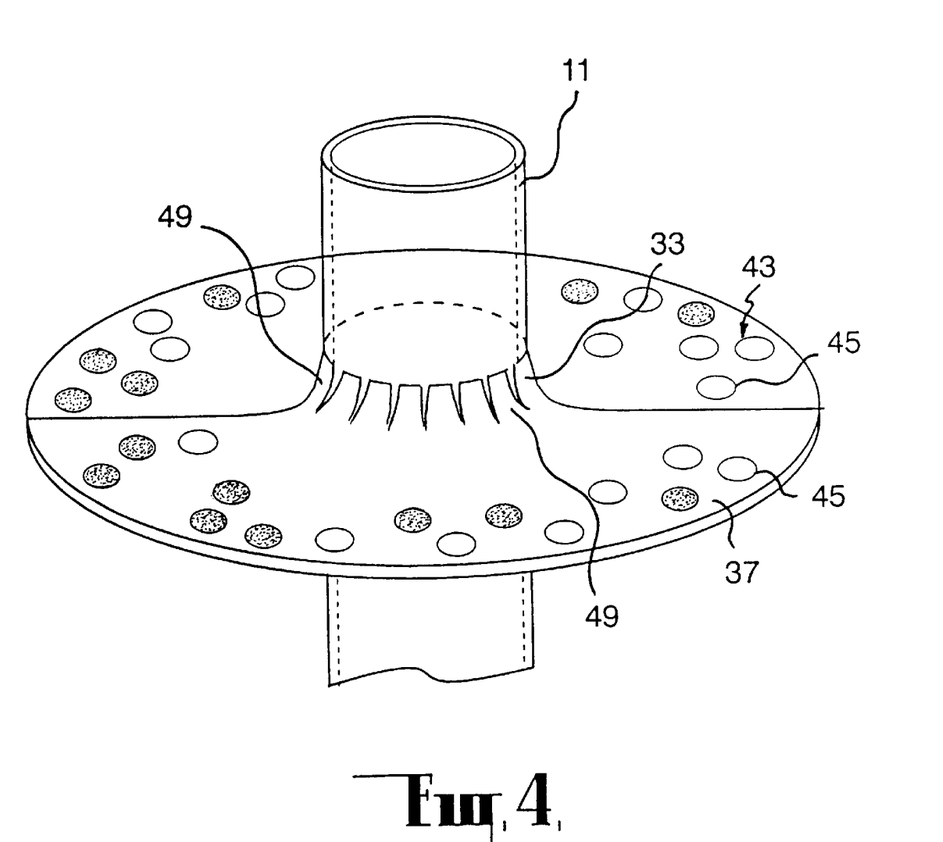
FIG. 4 is a schematic perspective view of a termite barrier according to a second embodiment fitted onto a conduit.

Referring now to FIG. 4 of the drawings, the termite barrier according to the second embodiment is similar to the termite barrier according to the first embodiment and so the same reference numerals will be used to identify similar features. The second embodiment is, however, different to the first embodiment in the construction of the central sleeve 33. In this embodiment, the central sleeve 33 comprises a plurality of resiliently deflectable sleeve segments 49, as shown in the drawing. The segments are formed by making radial cuts in the radially inner portion of the body 31 surrounding a central aperture. The central aperture is of lesser diameter than the external diameter of the conduit 11 and so fitting of the body onto the conduit 11 causes the resilient segments to deflect laterally in the manner shown in the drawing to form the sleeve 33. With this arrangement, the resilient nature of the sleeve segments 49 are in pressure engagement with the perimeter of the conduit 11.

Figure 5:
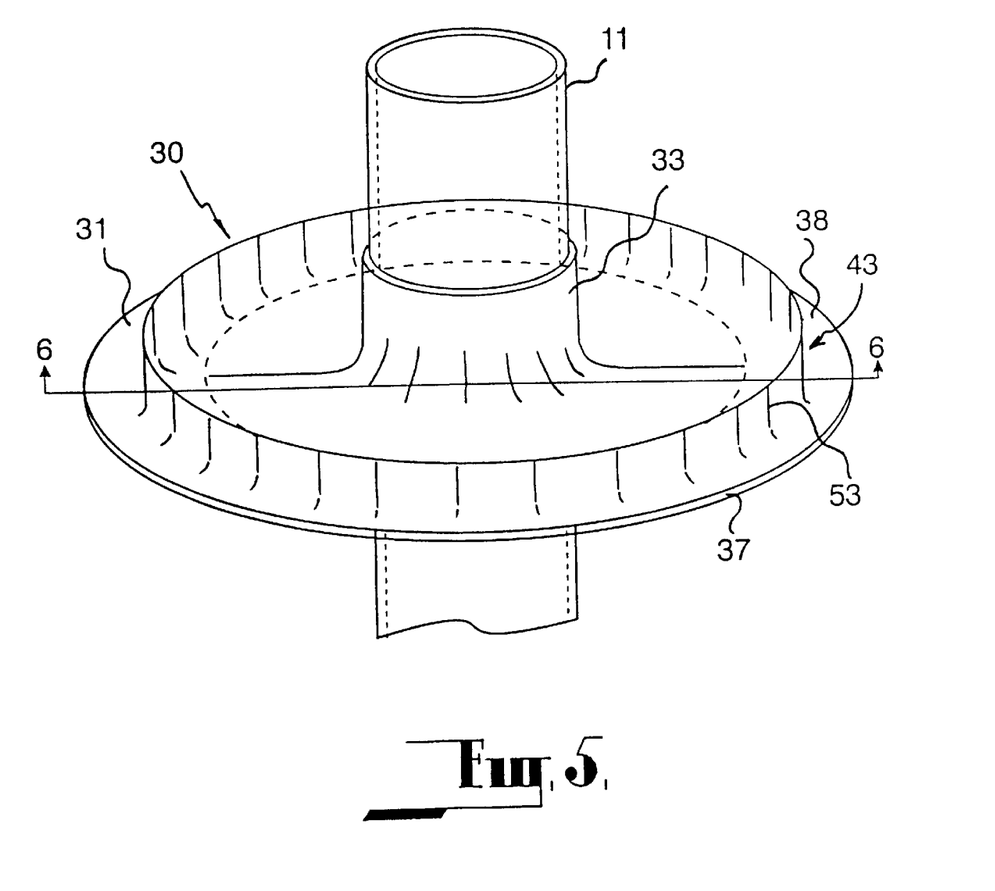
FIG. 5 is a schematic view of a termite barrier according to a third embodiment fitted onto a conduit.
Figure 6:
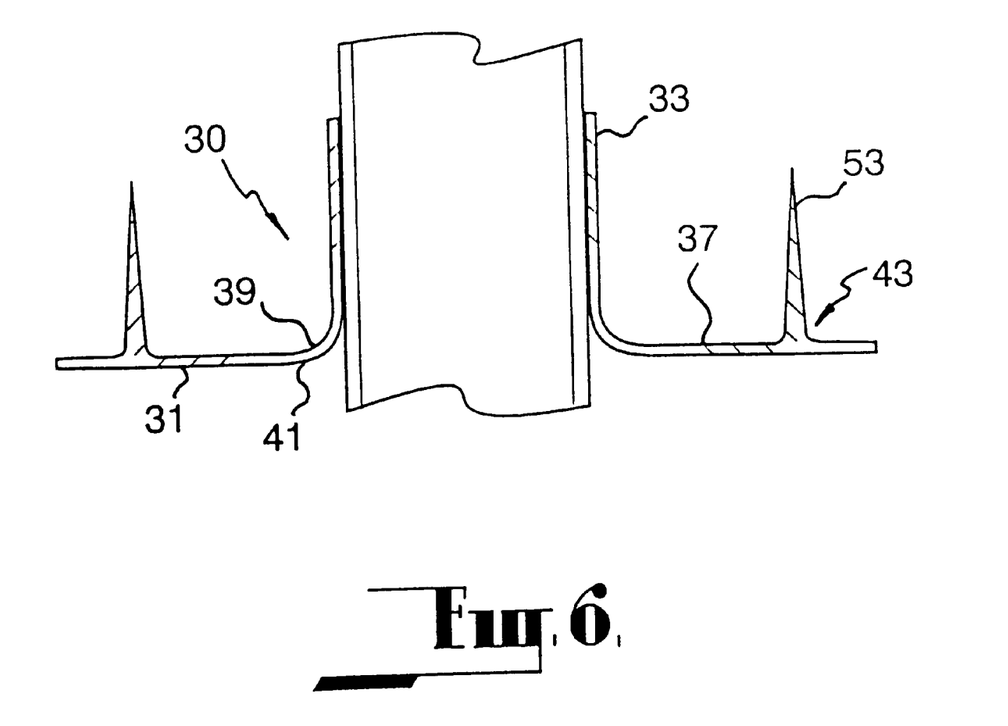
FIG. 6 is a cross sectional view along the line 6—6 of FIG. 5.

Referring now to FIGS. 5 and 6 of the drawings, the termite barrier 30 according to the third embodiment is also similar to the termite barrier of the first embodiment and corresponding numerals are used to identify similar features. In this embodiment, however, the formation 43 provided on the flange portion 37 of the body 31 comprises an annular rib 53. The annular rib is provided on one face 38 of the flange portion 37 in this embodiment, although it is certainly possible that an annular rib could be provided on both sides.

The annular rib provides a key between the flange portion 37 and the concrete to ensure gripping engagement between the concrete and the flange portion.

Figure 7:
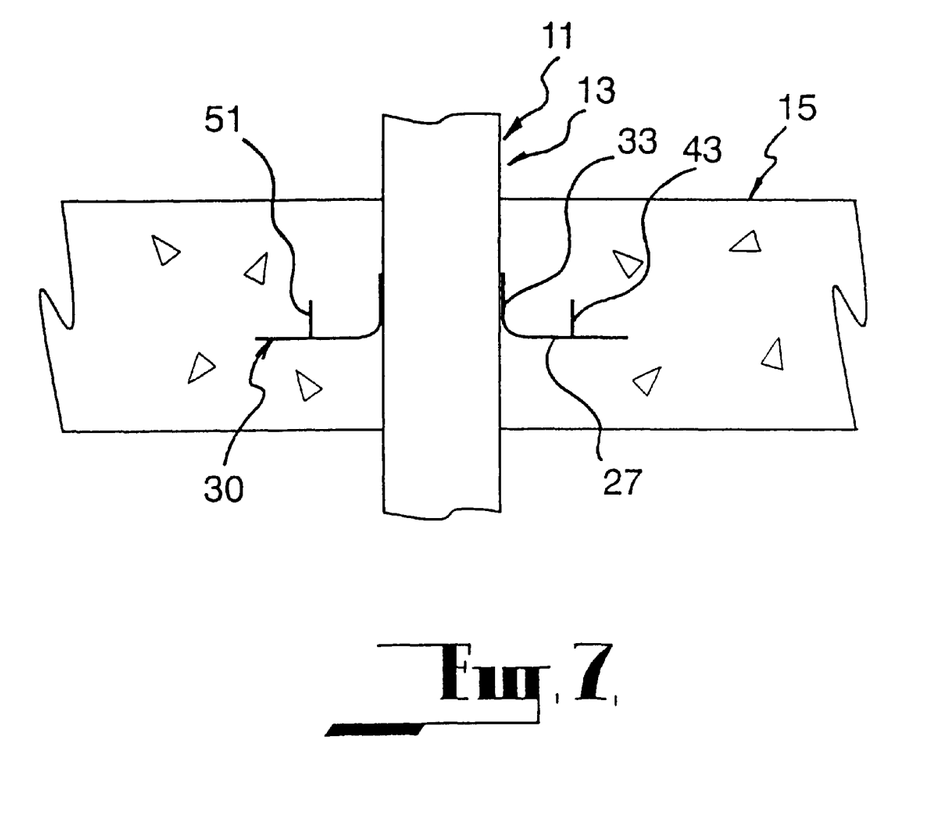
FIG. 7 is a schematic view of the termite barrier of FIG. 5 in one mode of installation about a conduit extending through a concrete slab.

FIG. 7 shows the termite barrier 30 according to the third embodiment in one mode of installation about a conduit 11 in concrete slab 15 In this mode of installation, the flange portion 37 is embedded entirely in the concrete of the slab.

Figure 8:
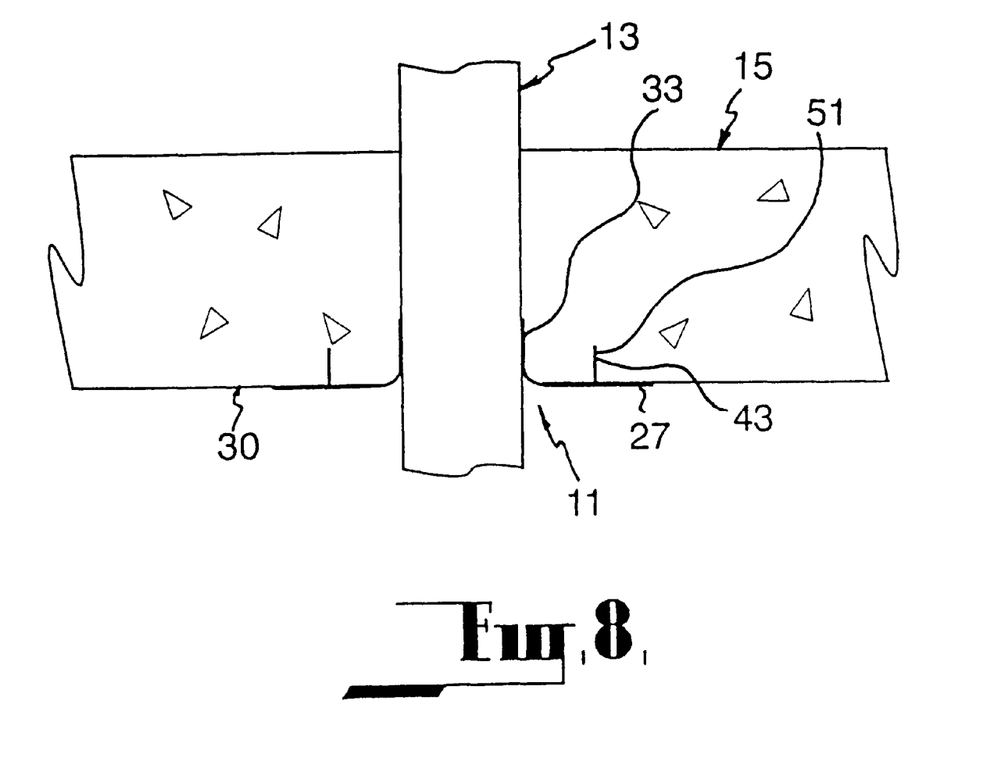
FIG. 8 is schematic view of the termite barrier of FIG. 5 in another mode of installation about a conduit extending through a concrete slab.

FIG. 8 shows the termite barrier 30 according to the third embodiment in another mode of installation in which the flange portion 37 is only partly embedded in the concrete of the slab 15. In this mode of installation, the flange portion 37 is positioned adjacent the underside of the slab with the annular rib 53 embedded in the concrete of the slab. This arrangement serves to block the passage of termites between the conduit 11 and the concrete slab even though only part of the flange portion is embedded in the concrete.

Figure 9:
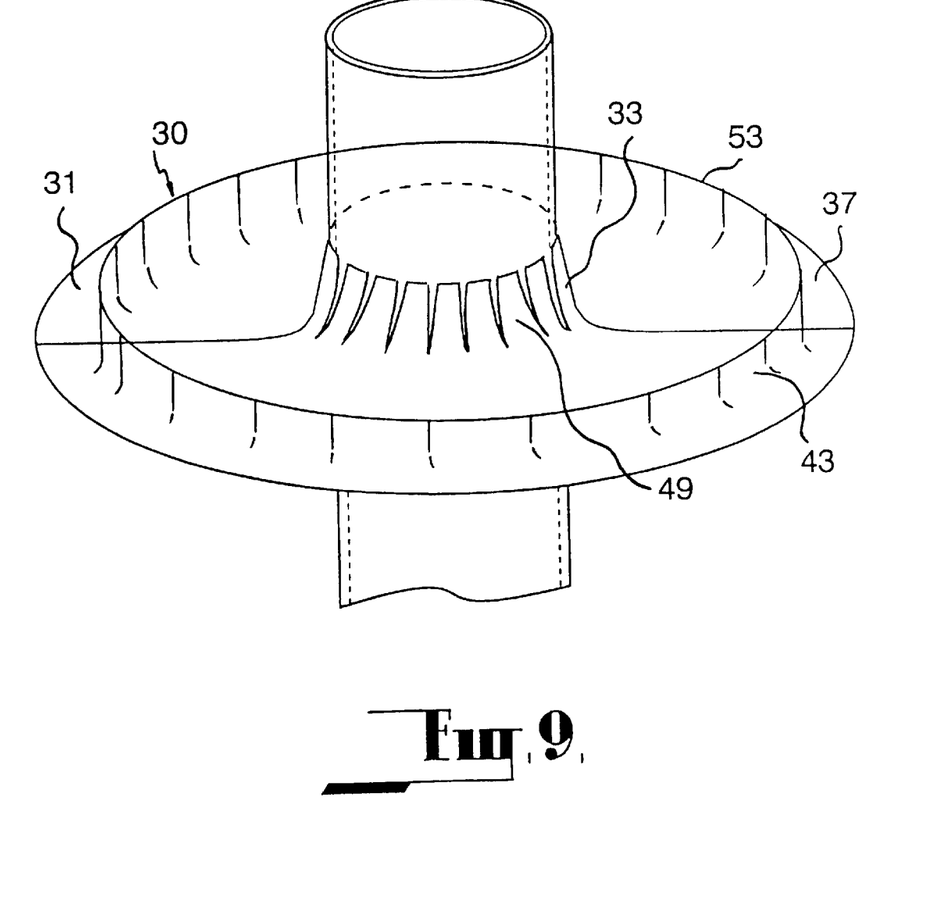
FIG. 9 is a schematic perspective view of a termite barrier according to a fourth embodiment fitted onto a conduit.

Referring now to FIG. 9 of the drawings, the termite barrier according to a fourth embodiment is similar to the termite barrier of the second embodiment except for the construction of the central sleeve 33. In this embodiment, the central sleeve is formed of sleeve segments 49 in a similar fashion to the central sleeve of the second embodiment.

It should be appreciated that the scope of the invention is not limited to the scope of the embodiments described.

What is claimed is:

1. A termite barrier comprising a body having an inner peripheral portion defining an aperture extending therethrough to sealingly receive an object therein and an outer peripheral portion adapted to be integrally secured to a concrete structure, the outer peripheral portion being provided with means for gripping engagement to the concrete structure, wherein the means for gripping engagement comprises at least one hole through the outer peripheral portion for receiving concrete flow therethrough to provide keying between the outer peripheral portion and concrete.

2. A termite barrier according to claim 1 wherein the aperture is dimensioned to provide a sufficiently close fit between the body and the conduit to prevent the passage of termites through the aperture.

3. A termite barrier according to claim 1 wherein the body is adapted to received the object in sealing engagement therewith.

4. A termite barrier according to claim 3 wherein said sealing engagement is provided by frictional engagement.

5. A termite barrier according to claim 3 wherein said sealing engagement is provided by clamping engagement.

6. A termite barrier according to claim 1 wherein the body includes a sleeve which defines the aperture.

7. A termite barrier according to claim 6 wherein the sleeve is adapted to be clamped in pressure engagement with the object about the entire periphery of the object.

8. A termite barrier according to claim 6 wherein the sleeve is adapted to frictionally engage the object.

9. A termite barrier according to claim 8 wherein the sleeve is of resiliently flexible construction.

10. A termite barrier according to claim 9 wherein the sleeve comprises a plurality of resiliently deflectable sleeve segments.

11. A termite barrier according to claim 6 wherein the body includes a transition region between the sleeve and the flange portion, said transition region presenting a curved surface on the lower side thereof to deter physical gripping thereof by termites.

12. A termite barrier according to claim 1 wherein the outer peripheral portion and the inner peripheral portion are of integral construction.

13. A termite barrier according to claim 1, in combination with a building having a concrete slab and an object extending through the slab wherein the termite barrier is installed between the slab and the object.

14. A termite barrier comprising a body having an inner peripheral portion defining an aperture extending therethrough to sealingly receive an object therein and an outer peripheral portion adapted to be integrally secured to a concrete structure, the outer peripheral portion being provided with means for gripping engagement to the concrete structure, wherein the outer peripheral portion is provided with a rib formation which facilitates gripping engagement between the outer peripheral portion and the concrete structure.

15. A termite barrier according to claim 14 wherein the rib formation comprises at least one recess in the outer peripheral portion.

16. A termite barrier according to claim 14 wherein the rib formation comprises at least one protrusion on the outer peripheral portion.

17. A termite barrier according to claim 16 wherein the outer peripheral portion has a pair of opposed surfaces of generally planar form, the rib formation being on at least one of the opposed surfaces.

18. In combination with a building structure incorporating a ground level or near ground level concrete structure having an opening therein through which an object (such as a conduit) extends, a termite barrier comprising a body having an inner peripheral portion defining an aperture extending therethrough which receives the object in sealing engagement therewith and an outer peripheral portion integrally secured to a concrete structure, the outer peripheral portion being provided with means for gripping engagement to the concrete structure.

19. A method of establishing a termite barrier between a concrete structure having an opening therein and an object extending through the opening, the termite barrier comprising a body having an inner peripheral portion defining an aperture extending therethrough to receive the object and an outer peripheral portion provided with means for gripping engagement to the concrete structure, the method including the acts of embedding at least part of the flange portion in the concrete structure during pouring of the concrete thereof such that the means for gripping engagement engages the concrete structure, and positioning the object in the aperture in sealing engagement therewith.

* * * * *